US009983179B2

(12) United States Patent
Narukami

(10) Patent No.: US 9,983,179 B2
(45) Date of Patent: May 29, 2018

(54) GAS CHROMATOGRAPH

(71) Applicant: HORIBA STEC, CO., LTD., Kyoto (JP)

(72) Inventor: Shoji Narukami, Kyoto (JP)

(73) Assignee: HORIBA STEC, CO., LTD., Kyoto (JP)

( * ) Notice: Subject to any disclaimer, the term of this patent is extended or adjusted under 35 U.S.C. 154(b) by 226 days.

(21) Appl. No.: 14/891,686

(22) PCT Filed: Dec. 4, 2014

(86) PCT No.: PCT/JP2014/082127
§ 371 (c)(1),
(2) Date: Nov. 17, 2015

(87) PCT Pub. No.: WO2015/083794
PCT Pub. Date: Jun. 11, 2015

(65) Prior Publication Data
US 2016/0097747 A1  Apr. 7, 2016

(30) Foreign Application Priority Data

Dec. 5, 2013  (JP) .................................. 2013-252548

(51) Int. Cl.
*G01N 30/68* (2006.01)
*G01N 30/84* (2006.01)
*G01N 30/02* (2006.01)

(52) U.S. Cl.
CPC ............. *G01N 30/68* (2013.01); *G01N 30/84* (2013.01); *G01N 2030/025* (2013.01); *G01N 2030/8435* (2013.01)

(58) Field of Classification Search
None
See application file for complete search history.

(56) References Cited

U.S. PATENT DOCUMENTS 4,842,825 A * 6/1989 Martin ................... G01N 31/12
422/80
5,766,954 A 6/1998 Freedman et al.
(Continued)

FOREIGN PATENT DOCUMENTS

JP  52-52693  4/1977
JP  9-145674  6/1997
(Continued)

OTHER PUBLICATIONS

Watanabe et al., "Simplification of determination method for standard materials using post-column reaction GC/FID", Talanta, Mar. 24, 2007, pp. 1655-1658, vol. 72.
(Continued)

*Primary Examiner* — Paul West
*Assistant Examiner* — Mark A Shabman
(74) *Attorney, Agent, or Firm* — Greenblum & Bernstein, P.L.C.

(57) ABSTRACT

In order to provide a gas chromatograph in which any adverse effects on a reduction reaction unit that are caused by the degradation of a reduction catalyst, and any adverse effects on an analyzing unit are prevented, a gas chromatograph is provided with: a column that, by causing a sample gas to pass through itself, is able to separate constituents for measurement that are contained in the sample gas; an oxidation reaction unit that uses an oxidizing gas to oxidize the sample gas that has passed through the column so as to create an oxidation sample gas; a reduction reaction unit that uses a reducing gas to reduce the oxidation sample gas created by the oxidation reaction unit so as to create an oxidation reduction sample gas; and an analyzing unit that analyzes the sample gas.

5 Claims, 7 Drawing Sheets

(56) References Cited

U.S. PATENT DOCUMENTS

| | | | | |
|---|---|---|---|---|
| 8,104,326 B2* | 1/2012 | Tipler | ............... | G01N 30/30 |
| | | | | 73/23.36 |
| 2003/0164312 A1* | 9/2003 | Prohaska | ........... | G01N 27/4045 |
| | | | | 205/783.5 |
| 2014/0219868 A1* | 8/2014 | Sasaki | ................ | G01N 27/626 |
| | | | | 422/54 |

FOREIGN PATENT DOCUMENTS

| JP | 9-508474 | 8/1997 |
|---|---|---|
| JP | 2013-68501 | 4/2013 |

OTHER PUBLICATIONS

International Search Report, with English-language translation thereof, for PCT/JP2014/082127, dated Mar. 10, 2015.

\* cited by examiner

GAS CHROMATOGRAPH

TECHNICAL FIELD

This invention relates to a gas chromatograph that analyzes constituents of a sample gas of an organic compound and the like.

TECHNICAL BACKGROUND

The gas chromatograph described in Patent document 1 is one of this type of gas chromatograph.

The gas chromatograph described in Patent document 1 is formed by connecting together in series an oxidization reaction unit in which is housed an oxidization catalyst that oxidizes a sample gas using an oxidizing gas so as to create an oxidation sample gas, a reduction reaction unit in which is housed a reduction catalyst that reduces the oxidation sample gas using a reducing gas so as to create an oxidation reduction sample gas, and an analyzing unit that analyzes predetermined constituents contained in the sample gases.

DOCUMENTS OF THE PRIOR ART

Patent Documents

[Patent document 1] Japanese Unexamined Patent Application (JP-A) No. 2013-68501

DISCLOSURE OF THE INVENTION

Problems to be Solved by the Invention

In order to determine whether there is any degradation in the catalysts, after the oxidation sample gas has been created by the oxidation reaction unit, it is introduced in some cases into the analyzing unit without firstly being reduced by the reduction reaction unit.

This type of gas chromatograph performs detections by switching between a first connection mode in which, as is shown in FIG. 7 (a), the oxidation reaction unit is connected to the reduction reaction unit and the reduction reaction unit is connected to a concentration detection device, and oxidation reduction sample gas is introduced into the concentration detection device, and a second connection mode in which, as is shown in FIG. 7 (b), the oxidation reaction unit is connected to the concentration detection device, and oxidation sample gas is introduced into the concentration detection device.

Here, because the reduction reaction unit is heated when it is used, it is not possible to immediately cool down the reduction reaction unit even if the gas chromatograph system has been stopped. Because of this, even after the gas chromatograph system has been stopped, oxygen contained in the oxidizing gas reacts in the reduction reaction unit with hydrogen contained in the reducing gas so as to create water.

However, if the system is stopped while in the first connection mode, the problem arises that the water that has been created in the reduction reaction unit flows into the analyzing unit, so that the detection instruments and the like that are provided in the analyzing unit corrode and malfunction.

On the other hand, if the gas chromatograph system is stopped in the second connection mode in which the reduction reaction unit is not connected to the analyzing unit, because the reduction reaction unit is isolated from the flow path and is independent, the problem arises that the atmosphere inside the reduction reaction unit changes to an oxidizing atmosphere, so that the reduction catalyst becomes oxidized and its catalytic activity is reduced.

The present invention was conceived in order to solve all of the above-described problems, and it is an object thereof to provide a gas chromatograph in which any adverse effects on the reduction reaction unit that are caused by the degradation of the reduction catalyst, and any adverse effects on the analyzing unit that are caused by the detection instruments and the like corroding and malfunctioning are prevented.

Means for Solving the Problem

The gas chromatograph according to the present invention is provided with: a column that, by causing a sample gas to pass through itself, is able to separate constituents to be measured that are contained in the sample gas; an oxidation reaction unit that, by using an oxidizing gas, oxidizes the sample gas that has passed through the column, and creates an oxidation sample gas; a reduction reaction unit that, by using a reducing gas, reduces the oxidation sample gas created by the oxidation reaction unit, and creates an oxidation reduction sample gas; and an analyzing unit that analyzes the sample gas, wherein the gas chromatograph is constituted to be able to switch between a first connection mode in which the oxidation reaction unit is connected to the reduction reaction unit, and the reduction reaction unit is connected to the analyzing unit, and the oxidation reduction sample gas is introduced into the analyzing unit, and a second connection mode in which the oxidation reaction unit is connected to the analyzing unit, and the oxidation sample gas is introduced into the analyzing unit, and wherein there is further provided a reducing gas supply pipe that, in both the first connection mode and the second connection mode, is connected to the reduction reaction unit and supplies the reducing gas to the reduction reaction unit.

According to the above-described structure, because the reducing gas supply pipe is connected to the reduction reaction unit in both the first connection mode and the second connection mode, even after the system of the gas chromatograph has been stopped, it is possible to supply reducing gas from the reducing gas supply pipe to the reduction reaction unit, and to purge the reduction reaction unit with this reducing gas, and to thereby remove any residual oxidizing gas from the reduction reaction unit. Because of this, in either of the above-described connection modes, it is possible to prevent water from being created in the reduction reaction unit, and to thereby prevent a detection instrument or the like that are provided in the analyzing unit from becoming corroded.

Moreover, because the reducing gas supply pipe is connected to the reduction reaction unit in the second connection mode as well, reducing gas can be made to flow from the reducing gas supply pipe into the reduction reaction unit, so that the atmosphere inside the reduction reaction unit is kept as a reducing atmosphere and any oxidation of the reduction catalyst can be prevented.

Furthermore, because the reducing gas supply pipe is connected to the reduction reaction unit, it is possible to prevent any decrease in the linear velocity of the reducing gas supplied to the reduction reaction unit, and to prevent any broadening of the peak of the sample gas detected by the detection instrument provided in the analyzing unit so that an accurate analysis can be made.

Note that the aforementioned connections may be either direct connections or indirect connections.

As a specific aspect of the present invention, it is also possible for there to be further provided an inert gas supply pipe that supplies inert gas to the reduction reaction unit.

By employing this type of structure, it is possible to prevent the concentration detection device from becoming corroded by using an extremely safe, easily-handled inert gas, and any oxidation of the reduction catalyst can be prevented.

As another specific aspect of the present invention, it is also possible for a structure to be employed in which the connection between the inert gas supply pipe and the reduction reaction unit is blocked, while in the second connection mode, the inert gas supply pipe and the reduction reaction unit are connected to each other.

By employing this type of structure, because the flow path along which the inert gas flows can also be switched so as to match the switching between the first connection mode and the second connection mode, compared with when the flow path along which the inert gas flows is switched separately from the first connection mode and the second connection mode, the apparatus structure can be made extremely convenient to use.

As yet another specific aspect of the present invention, it is also possible for the analyzing unit to have a flame ionization detector, and for there to be further provided a makeup gas supply pipe that supplies makeup gas to the analyzing unit, and for a structure to be employed in which, in the first connection mode, the connection between the makeup gas supply pipe and the reduction reaction unit is blocked, while in the second connection mode, the makeup gas supply pipe and the reduction reaction unit are connected to each other.

By employing this type of structure, because it is possible to use the makeup gas which is used in the flame ionization detector provided in the analyzing unit as the inert gas, it is possible to prevent any adverse effects on the reduction reaction unit and the concentration detection device by means of a lower-cost and simpler structure compared with when inert gas is prepared separately.

As yet another specific aspect of the present invention, it is also possible for the analyzing unit to have a flame ionization detector, and for the reducing gas to be hydrogen.

By employing this type of structure, because the hydrogen that is used as the fuel of the flame ionization detector provided in the analyzing unit can be used as the reducing gas, it is possible to prevent any adverse effects on the reduction reaction unit and the concentration detection device by means of a simple and low-cost apparatus structure.

Effects of the Invention

According to the present invention, it is possible to provide a gas chromatograph in which any adverse effects on the reduction reaction unit that are caused by the degradation of the reduction catalyst, and any malfunctioning of the concentration detection device are prevented.

BRIEF DESCRIPTION OF THE DRAWINGS

FIG. 2 (b) is an explanatory view showing a second connection mode in the gas chromatograph according to the first embodiment of the present invention.

FIG. 3 (b) is an explanatory view showing a second connection mode in the gas chromatograph according to the second embodiment of the present invention.

FIG. 4 (b) is an explanatory view showing a second connection mode in the gas chromatograph according to the third embodiment of the present invention.

FIG. 5 (b) is an explanatory view showing a second connection mode in the gas chromatograph according to the fourth embodiment of the present invention.

FIG. 6 (b) is an explanatory view showing a second connection mode in the gas chromatograph according to the fifth embodiment of the present invention.

FIG. 7 (b) is an explanatory view showing a second connection mode in a conventional gas chromatograph.

DESCRIPTION OF THE REFERENCE NUMERALS

1 . . . Gas chromatograph
2 . . . Column
4 . . . Oxidation reaction unit
6 . . . Reducing gas supply pipe
7 . . . Reduction reaction unit
8 . . . Analyzing unit

BEST EMBODIMENTS FOR IMPLEMENTING THE INVENTION

First Embodiment

Figure 1:
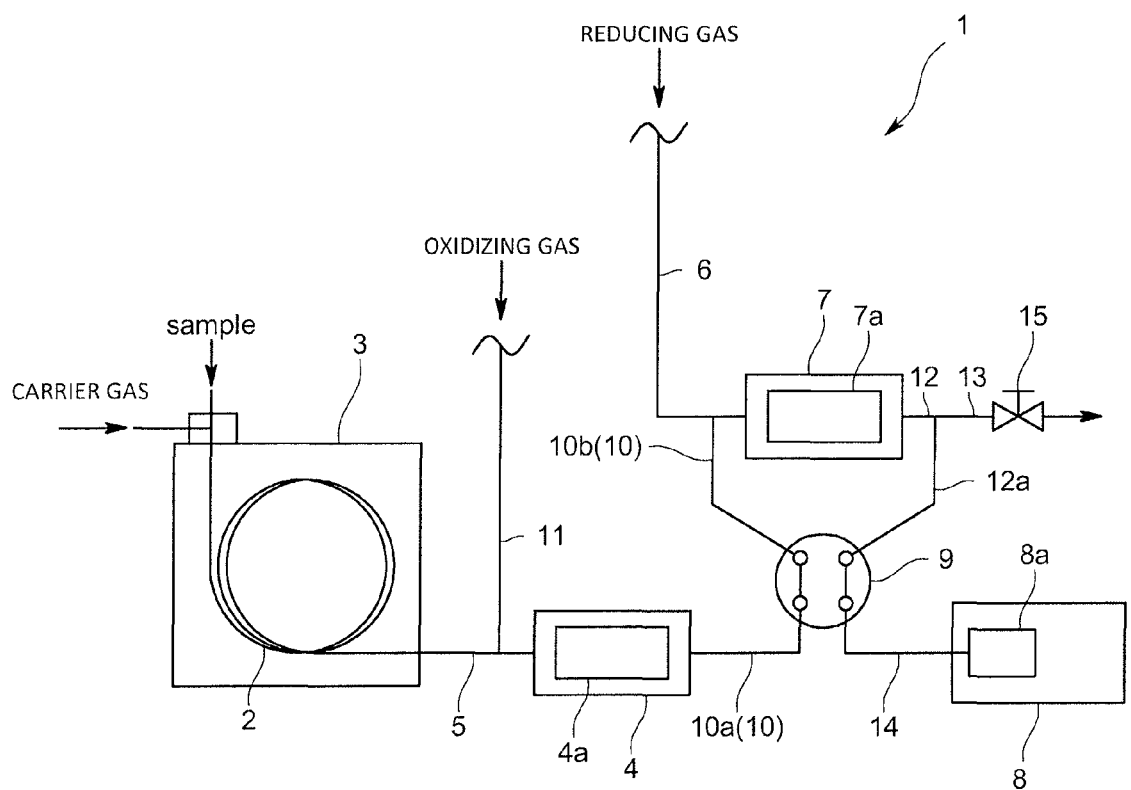
FIG. 1 is a schematic view of a gas chromatograph according to a first embodiment of the present invention.

As is shown in FIG. 1, a gas chromatograph 1 according to a first embodiment of the present invention is provided with a column 2 that, by causing a sample gas to pass through itself, is able to separate constituents for measurement that are contained in the sample gas, a thermostatic tank 3 inside which the column 2 is housed, an oxidation reaction unit 4 that uses an oxidizing gas to oxidize the sample gas that has passed through the column 2 so as to create an oxidation sample gas, a first supply pipe 5 that is connected to the oxidation reaction unit 4 and supplies the sample gas and the oxidizing gas thereto, a reduction reaction unit 7 that uses a reducing gas to reduce the oxidation sample gas created by the oxidation reaction unit 4 so as to create an oxidation reduction sample gas, a reducing gas supply pipe 6 that is connected to the reduction reaction unit 7 and supplies the reducing gas to this reduction reaction unit 7, an analyzing unit 8 that is used to analyze constituents of a sample gas, and a switching mechanism 9 that switches the connection mode of the flow path along which the sample gas flows.

The column 2 is, for example, a capillary column having a stationary phase coated on an internal wall of the pipe thereof. Carrier gas and sample gas are introduced into an end thereof that is located on the upstream side, while another end thereof, which is located on the downstream side, is connected to the first supply pipe 5. Note that a known suitable stationary phase that matches the type of sample can be used as the stationary phase, while an inert gas such as, for example, helium, argon or the like, or hydrogen gas, air or the like can be used as the carrier gas.

The first supply pipe 5 supplies sample gas and oxidizing gas to the oxidation reaction unit 4. An end portion on the upstream side thereof is connected to the column 2, while an end portion on the downstream side is connected to the oxidation reaction unit 4. An oxidizing gas supply pipe 11 that supplies oxidizing gas is connected to the first supply pipe 5.

The oxidizing gas supply pipe 11 supplies oxidizing gas to the oxidation reaction unit 4. An end portion on the upstream side thereof is connected to an oxidizing gas supply unit (not shown), while an end portion on the downstream side is connected to the first supply pipe 5. For example, air or the like is used as the oxidizing gas.

The oxidation reaction unit 4 oxidizes sample gas so as to create oxidation sample gas. The oxidation reaction unit 4 internally houses an oxidation reaction pipe (not shown) in which an oxidation catalyst 4a such as, for example, platinum, palladium or the like has been placed, and an oxidation reaction furnace (not shown) such as a heater that heats the oxidation reaction pipe. An end portion on the upstream side of the oxidation reaction pipe is connected to the first supply pipe 5, while an end portion on the downstream side thereof is connected to an oxidation sample gas extraction pipe 10. In the present embodiment, the oxidation catalyst 4a uses an oxidizing gas to convert the sample gas that has passed through the column 2 into an oxide (i.e., an oxidation sample gas) such as carbon dioxide or the like.

The oxidation sample gas extraction pipe 10 is used to extract the oxide sample gas created in the oxidation reaction unit 4. The oxidation sample gas extraction pipe 10 is provided with a first oxidation sample gas extraction pipe 10a and a second oxidation sample gas extraction pipe 10b. An end portion on the upstream side of the first oxidation sample gas extraction pipe 10a is connected to the oxidation reaction unit 4, while an end portion on the downstream side of the second oxidation sample gas extraction pipe 10b is connected to the reducing gas supply pipe 6.

The reducing gas supply pipe 6 supplies reducing gas to the reduction reaction unit 7, and is provided between the switching mechanism 9 and either the reduction reaction unit 7 or the reduction catalyst 7a that is installed in the reduction reaction unit 7. In the present embodiment, an end portion on the upstream side of the reducing gas supply pipe 6 is connected to a reducing gas supply unit (not shown) which supplies reducing gas, while an end portion on the downstream side thereof is connected to the reduction reaction unit 7. For example, hydrogen or the like is used as the reducing gas. In addition, the second sample gas extraction pipe 10b is connected partway along the reducing gas supply pipe 6.

The reduction reaction unit 7 reduces the oxidation sample gas so as to create an oxidation reduction sample gas, and is internally provided with a reduction reaction pipe in which a reduction catalyst 7a such as, for example, nickel or the like is placed, and with a reduction reaction furnace such as a heater or the like that heats the reduction reaction pipe. An end portion on the upstream side of the reduction reaction pipe is connected to the reducing gas supply pipe 6, while an end portion on the downstream side thereof is connected to an oxidation reduction sample gas extraction pipe 12. In the present embodiment, the reduction catalyst 7a uses this reducing gas to convert the oxidation sample gas into a hydroxide (i.e., an oxidation reduction sample gas) such as, for example, methane.

An end portion on the upstream side of the oxidation reduction sample gas extraction pipe 12 is connected to the reduction reaction unit 7, while an end portion of the downstream side thereof branches off into two branch paths. One branch path is connected to a first oxidation reduction sample gas extraction pipe 12a along which the oxidation reduction sample gas flows, while the other branch path is connected to a discharge pipe 13 that discharges gas that has passed through the reduction reaction unit 7 to the outside. A shut-off valve 15 is provided on the discharge pipe 13.

The analyzing unit 8 analyzes the constituents of a sample gas, and has a concentration detection device 8a that detects concentrations of predetermined constituents contained in an oxidation sample gas or an oxidation reduction sample gas, and a concentration calculation unit (not shown) that, based on the concentrations of predetermined constituents detected by the concentration detection device 8a, calculates the concentrations of the constituents contained in a sample gas that are to be measured.

The concentration detection device 8a may be, for example, a thermal conductivity detector (TCD), or a flame ionization detector (FID) that detects predetermined compounds by measuring an ionization current that has been ionized by a hydrogen flame. An analysis pipe 14 along which the oxidation sample gas or oxidation reduction sample gas flows is connected to the concentration detection device 8a.

The switching mechanism 9 switches the connection mode of the flow path along which the sample gas flows. The switching mechanism 9 switches between a first connection mode in which the oxidation reaction unit 4 is connected to the reducing gas supply pipe 6 or the reduction reaction unit 7, and the reduction reaction unit 7 is connected to the concentration detection device 8a, while the connection between the oxidation reaction unit 4 and the concentration detection device 8a is blocked so that oxidation reduction sample gas is introduced into the concentration detection device 8a, and a second connection mode in which the oxidation reaction unit 4 is connected to the concentration detection device 8a, while the connection between the oxidation reaction unit 4 and the reducing gas supply pipe 6 or the reduction reaction unit 7 is blocked so that oxidation sample gas is introduced into the concentration detection device 8a.

This switching mechanism 9 is provided with a 4-way valve, and switches the connections between the first oxidation sample gas extraction pipe 10a, the second oxidation sample gas extraction pipe 10b, the first oxidation reduction sample gas extraction pipe 12a, and the analysis pipe 14. The 4-way valve is provided with pipe holes (not shown) to which the aforementioned plurality of pipes are individually attached, valve bodies (not shown) that are placed above the pipe holes and open or close the pipes, toroidal coils (not shown) that are located above the valve bodies, fixed iron cores that are placed inside the rings of the toroidal coils, and movable cores that are placed between the fixed iron cores and the valve bodies and are linked to the valve bodies.

When current flows through the coil, the fixed iron core and the movable core are magnetized such that they attract each other. As a result, the movable core causes the valve body to move so that the pipe is opened or closed. Note that the mechanism by which the movable core moves the valve body may be a direct-drive type of mechanism in which the valve body is moved mechanically, or a pilot-type of mechanism in which fluid pressure differences are used to move the valve body.

Operations of the switching mechanism 9 will now be described.

Figure 2A:
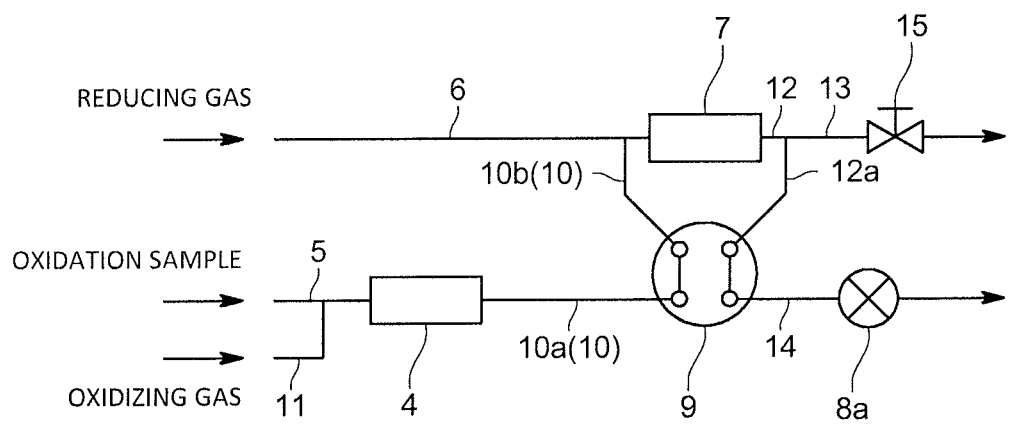
FIG. 2 (a) is an explanatory view showing a first connection mode in a gas chromatograph according to the first embodiment of the present invention.
Figure 2B:
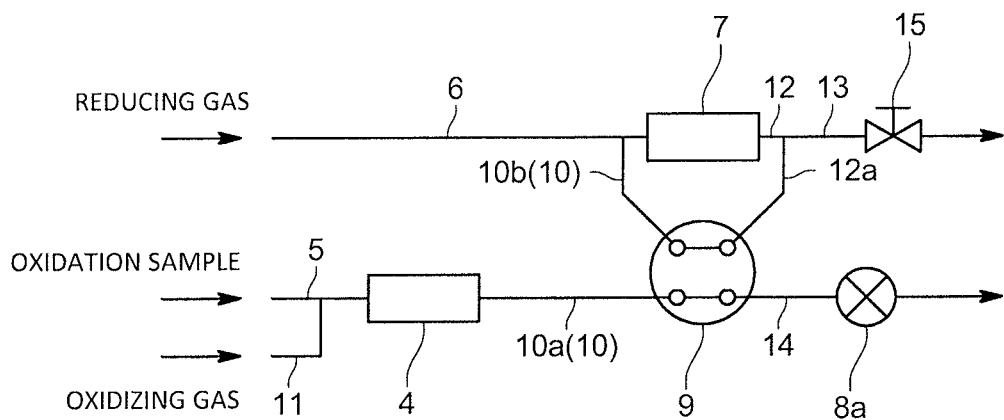

When the switching mechanism 9 switches to the first connection mode, as is shown in FIG. 2 (a), the valve bodies of the four-way valve are moved such that the first oxidation sample gas extraction pipe 10a is connected to the second oxidation sample gas extraction pipe 10b, and the first oxidation reduction sample gas extraction pipe 12a is connected to the analysis pipe 14. In addition, the connection between the first oxidation sample gas extraction pipe 10a and the analysis pipe 14 is blocked. Moreover, the shut-off valve 15 provided in the discharge pipe 13 is closed.

As a result of this, the oxidation reaction unit 4 is connected to the reduction reaction unit 7 via the first oxidation sample gas extraction pipe 10a and the second oxidation sample gas extraction pipe 10b. In addition, the reduction reaction unit 7 is connected to the concentration detection device 8a via the first oxidation reduction sample gas extraction pipe 12a and the analysis pipe 14.

As a consequence of this, oxidation sample gas is introduced into the reduction reaction unit 7, and reducing gas is also supplied to the reduction reaction unit 7. In the reduction reaction unit 7, the reduction catalyst 7a uses the reducing gas to reduce the oxidation sample gas and thereby create oxidation reduction sample gas. This oxidation reduction sample gas is then introduced into the concentration detection device 8a.

In contrast, when the switching mechanism 9 switches to the second connection mode, as is shown in FIG. 2 (b), the first oxidation sample gas extraction pipe 10a is connected to the analysis pipe 14, and the second oxidation sample gas extraction pipe 10b is connected to the first oxidation reduction sample gas extraction pipe 12a. Moreover, the shut-off valve 15 provided in the extraction pipe 13 is opened.

As a result of this, the oxidation reaction unit 4 is connected to the concentration detection device 8a via the first oxidation sample gas extraction pipe 10a and the analysis pipe 14.

As a consequence of this, oxidation sample gas is introduced into the concentration detection device 8a. In addition, reducing gas is supplied to the reduction reaction unit 7 via the reducing gas supply pipe 6, and the reducing gas that has passed through the reduction reaction unit 7 is discharged to the outside.

In the gas chromatograph 1 of the first embodiment which has the above-described structure, because the reducing gas supply pipe 6 is connected to the reduction reaction unit 7 in both the first connection mode and the second connection mode, even after the system of the gas chromatograph 1 has been stopped, it is possible to supply reducing gas from the reducing gas supply pipe 6 to the reduction reaction unit 7, and to purge the reduction reaction unit 7 with this reducing gas, and to thereby remove any residual oxidizing gas from the reduction reaction unit 7. Because of this, in either of the above-described connection modes, it is possible to prevent water from being created in the reduction reaction unit 7, and to thereby prevent the concentration detection device 8a from becoming corroded.

Moreover, because the reducing gas supply pipe 6 is connected to the reduction reaction unit 7 in the second connection mode as well, reducing gas can be made to flow from the reducing gas supply pipe 6 into the reduction reaction unit 7, so that the atmosphere inside the reduction reaction unit 7 is kept as a reducing atmosphere and any oxidation of the reduction catalyst 7a can be prevented.

Furthermore, because the reducing gas supply pipe 6 is directly connected to the reduction reaction unit 7, it is possible to prevent any decrease in the linear velocity of the reducing gas supplied to the reduction reaction unit 7, and to prevent any broadening of the peak of the sample gas detected by the concentration detection device 8a so that an accurate analysis can be made.

In addition, if the concentration detection device 8a is a flame ionization detector, then the hydrogen that serves as the fuel of the flame ionization detector can be used as the reducing gas, and it is possible to prevent any deterioration of the reduction reaction unit 7 and the concentration detection device 8a by means of a simple and low-cost apparatus structure.

Second Embodiment

Next, a gas chromatograph 1 according to a second embodiment of the present invention will be described. Note that the same symbols are used for portions that are the same as in the first embodiment, and any description of such portions is omitted.

In the gas chromatograph 1 according to the second embodiment, an inert gas supply pipe 20 that supplies an inert gas to the reduction reaction unit 7 in the second connection mode is also connected.

An end portion on the upstream side of the inert gas supply pipe 20 is connected to an inert gas supply unit (not shown), while an end portion on the downstream side thereof is connected to the reducing gas supply pipe 6. For example, a 3-way valve 21 is provided in the location of this latter connection. For example, argon or the like can be used for this inert gas.

Figure 3:
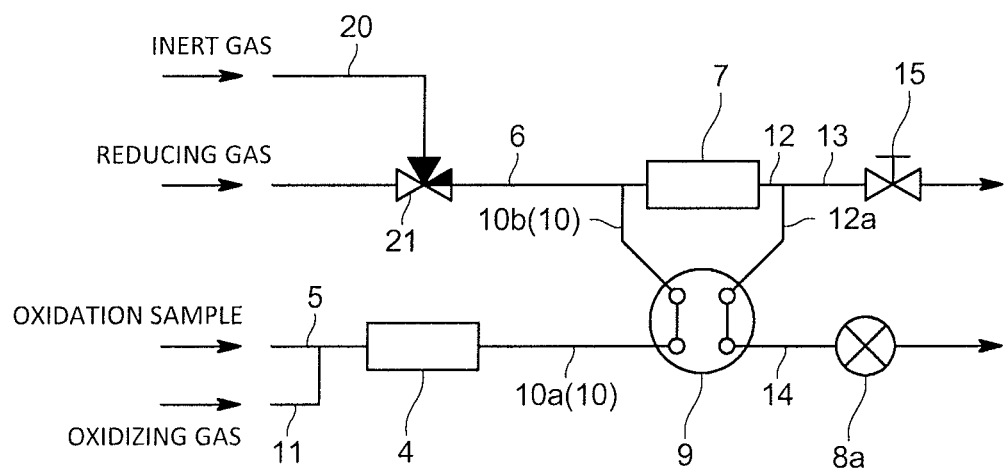
FIG. 3 (a) is an explanatory view showing a first connection mode in a gas chromatograph according to a second embodiment of the present invention.
Figure 3:
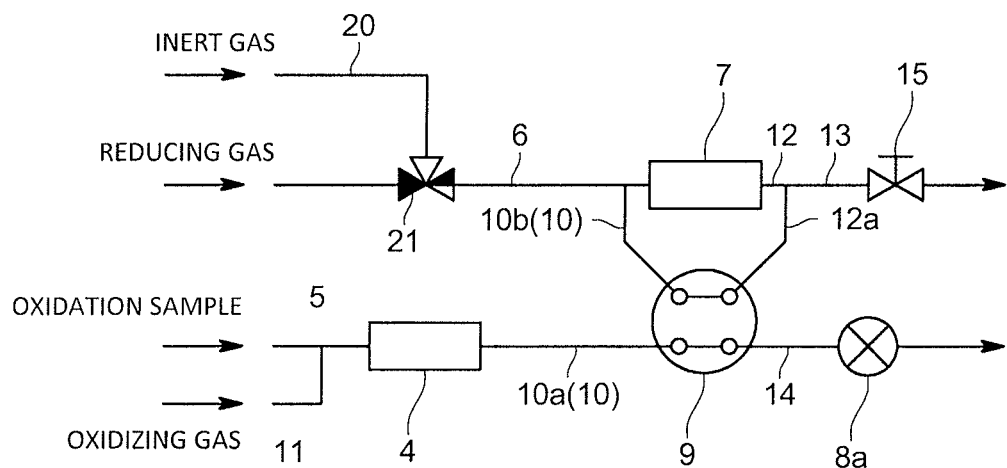

When the switching mechanism 9 switches to the first connection mode, in addition to the operations described in the first embodiment, as is shown in FIG. 3 (a), the 3-way valve 21 is operated such that the pipeline of the inert gas supply pipe 20 is closed, and the shut-off valve 15 provided in the discharge pipe 13 is also closed.

As a result of this, in the first connection mode, the connection between the inert gas supply pipe 20 and the reduction reaction unit 7 is blocked.

In contrast, when the switching mechanism 9 switches to the second connection mode, in addition to the operations described in the first embodiment, as is shown in FIG. 3 (b), the 3-way valve 21 is operated such that the pipeline of the inert gas supply pipe 20 is opened, and such that the reducing gas supply pipe 6 is closed. In addition, the shut-off valve 15 provided in the discharge pipe 13 is opened.

As a result of this, in the second connection mode, the connection between the inert gas supply pipe 20 and the reduction reaction unit 7 is blocked.

In the gas chromatograph 1 of the second embodiment which has the above-described structure, it is possible to prevent the concentration detection device 8a from becoming corroded using an extremely safe, easily-handled inert gas. In addition, any oxidation of the reduction catalyst 7a can be prevented in the first connection mode and the second connection mode.

Third Embodiment

Next, a gas chromatograph according to a third embodiment of the present invention will be described. Note that the same symbols are used for portions that are the same as in the first embodiment and the second embodiment, and any description of such portions is omitted.

In a gas chromatograph 1 according to the third embodiment, the inert gas supply pipe 20 is incorporated into a switching mechanism 30. Moreover, in the present embodiment, the first oxidation reduction sample gas extraction pipe 12 and the discharge pipe 13 are formed separately from each other.

The switching mechanism 30 is provided with a 6-way valve, and switches the connections between the first oxidation sample gas extraction pipe 10a, the second oxidation sample gas extraction pipe 10b, the inert gas supply pipe 20, the discharge pipe 13, the first oxidation reduction sample gas extraction pipe 12, and the analysis pipe 14. Note that because the specific structure of the 6-way valve is similar to that of the 4-way valve, a description thereof is omitted here.

Figure 4:
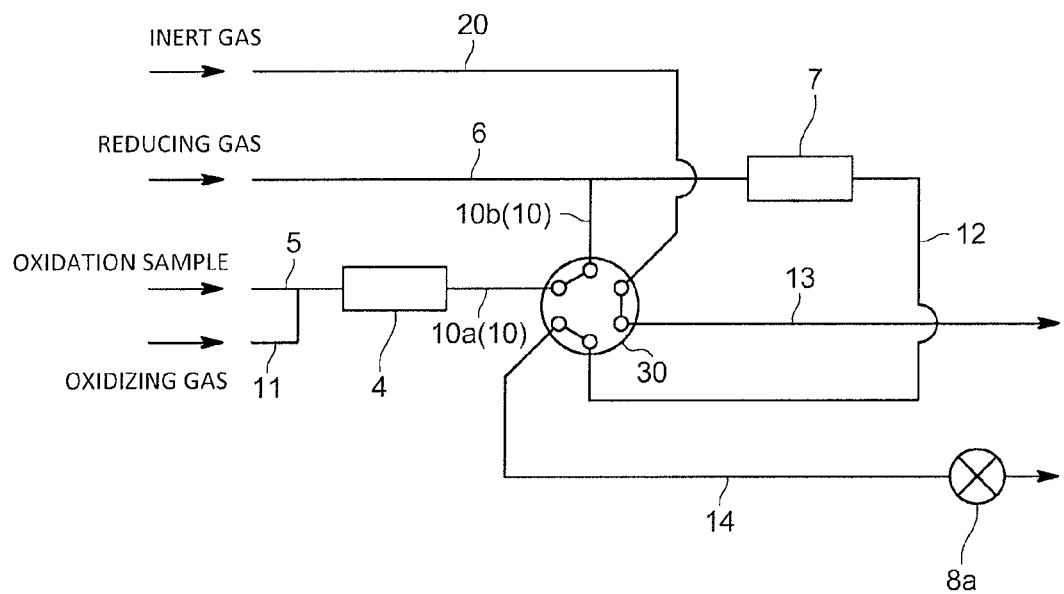
FIG. 4 (a) is an explanatory view showing a first connection mode in a gas chromatograph according to a third embodiment of the present invention.
Figure 4:
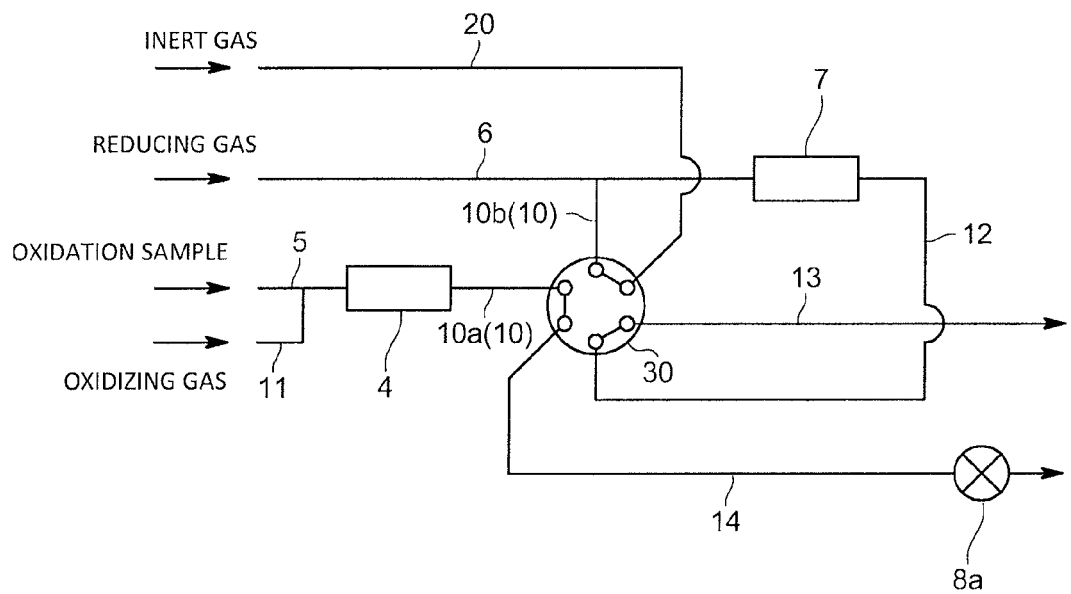

When the switching mechanism 30 switches to the first connection mode, as is shown in FIG. 4 (a), the first oxidation sample gas extraction pipe 10a is connected to the second oxidation sample gas extraction pipe 10b, the inert gas supply pipe 20 is connected to the discharge pipe 13, and the first oxidation reduction sample gas extraction pipe 12 is connected to the analysis pipe 14.

As a result of this, the oxidation reaction unit 4 is connected to the reduction reaction unit 7 via the first oxidation sample gas extraction pipe 10a and the second oxidation sample gas extraction pipe 10b. Moreover, the reduction reaction unit 7 is connected to the concentration detection device 8a via the first oxidation reduction sample gas extraction pipe 12 and the analysis pipe 14. In addition, the connection between the inert gas supply pipe 20 and the reduction reaction unit 7 is blocked.

As a consequence of this, oxidation sample gas is introduced into the reduction reaction unit 7, and reducing gas is also supplied to the reduction reaction unit 7 via the reducing gas supply pipe 6. The reduction catalyst 7a uses this reducing gas to reduce the oxidation sample gas and thereby create an oxidation reduction sample gas, and this oxidation reduction sample gas is introduced into the concentration detection device 8a. At this time, the inert gas is discharged to the outside via the inert gas supply pipe 20 and the discharge pipe 13.

In contrast, when the switching mechanism 30 switches to the second connection mode, as is shown in FIG. 4 (b), the first oxidation sample gas extraction pipe 10a is connected to the analysis pipe 14, the inert gas supply pipe 20 is connected to the second oxidation sample gas extraction pipe 10b, and the discharge pipe 13 is connected to the first oxidation reduction sample gas extraction pipe 12.

As a result of this, the oxidation reaction unit 4 is connected to the concentration detection device 8a via the first oxidation sample gas extraction pipe 10a and the analysis pipe 14. Moreover, the inert gas supply pipe 20 is connected to the reduction reaction unit 7.

As a consequence of this, oxidation sample gas is introduced into the concentration detection device 8a. Moreover, reducing gas is supplied to the reduction reaction unit 7 via the reducing gas supply pipe 6, and inert gas is also supplied to the reduction reaction unit 7 via the inert gas supply pipe 20. A gas mixture formed by the reducing gas and the inert gas then passes through the reduction reaction unit 7 and is discharged to the outside via the first oxidation reduction sample gas extraction pipe 12 and the discharge pipe 13.

In the gas chromatograph 1 of the third embodiment which has the above-described structure, because the flow path along which the inert gas flows can also be switched so as to match the switching between the first connection mode and the second connection mode, the apparatus structure can be made far more convenient to use compared with when the flow path along which the inert gas flows is switched separately from the first connection mode and the second connection mode.

Fourth Embodiment

Next, a gas chromatograph 1 according to a fourth embodiment of the present invention will be described. Note that the same symbols are used for portions that are the same as in the first embodiment, the second embodiment, and the third embodiment, and any description of such portions is omitted.

The gas chromatograph according to the fourth embodiment is a variant example of the gas chromatograph 1 of the third embodiment in that, instead of the inert gas supply pipe 20 along which an inert gas flows, there are provided a first makeup gas pipe 40 and a second makeup gas pipe 41 along which makeup gas flows. Moreover, the discharge pipe is not provided in the present embodiment. In addition, the concentration detection device 8a is a flame ionization detector.

The switching mechanism 42 is provided with the same type of 6-way valve as in the third embodiment, and switches the connections between the first oxidation sample gas extraction pipe 10a, the second oxidation sample gas extraction pipe 10b, the first oxidation reduction sample gas extraction pipe 12, the analysis pipe 14, the first makeup gas pipe 40, and the second makeup gas pipe 41.

The first makeup gas pipe 40 and the second makeup gas pipe 41 are pipes along which makeup gas flows. This makeup gas is used to raise the flow velocity of sample gas introduced into the flame ionization detector, and to improve the sensitivity of the detector. An end portion on the upstream side of the first makeup gas pipe 40 is connected to a makeup gas supply unit (not shown), while an end portion on the downstream side thereof is connected to the 6-way valve. An end portion on the upstream side of the second makeup pipe 41 is connected to the 6-way valve, while an end portion on the downstream side thereof is connected to the analysis pipe 14.

Figure 5:
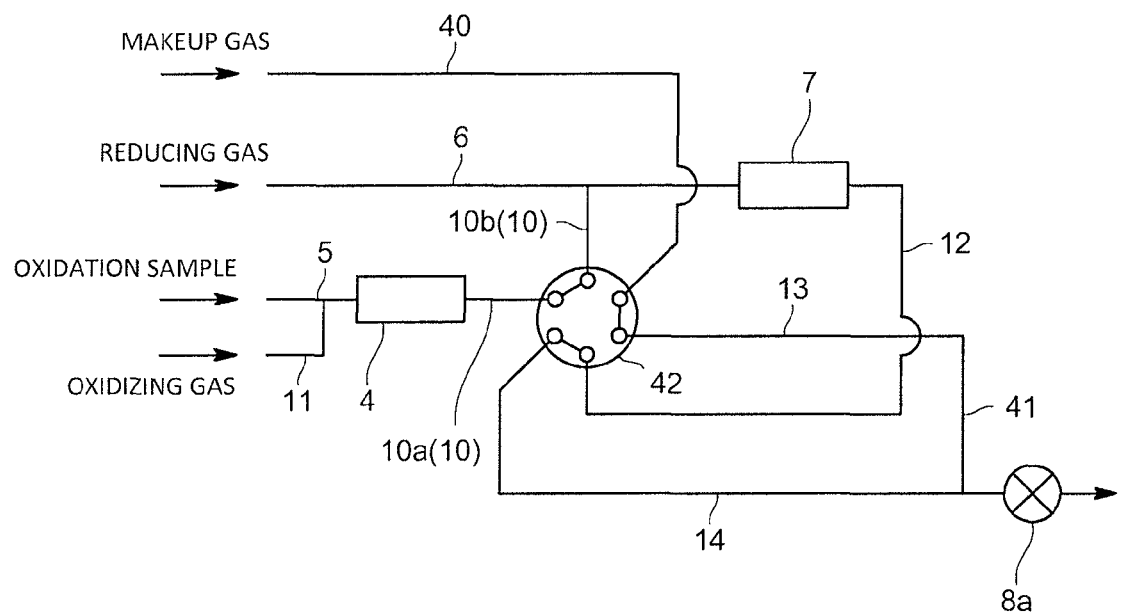
FIG. 5 (a) is an explanatory view showing a first connection mode in a gas chromatograph according to a fourth embodiment of the present invention.
Figure 5:
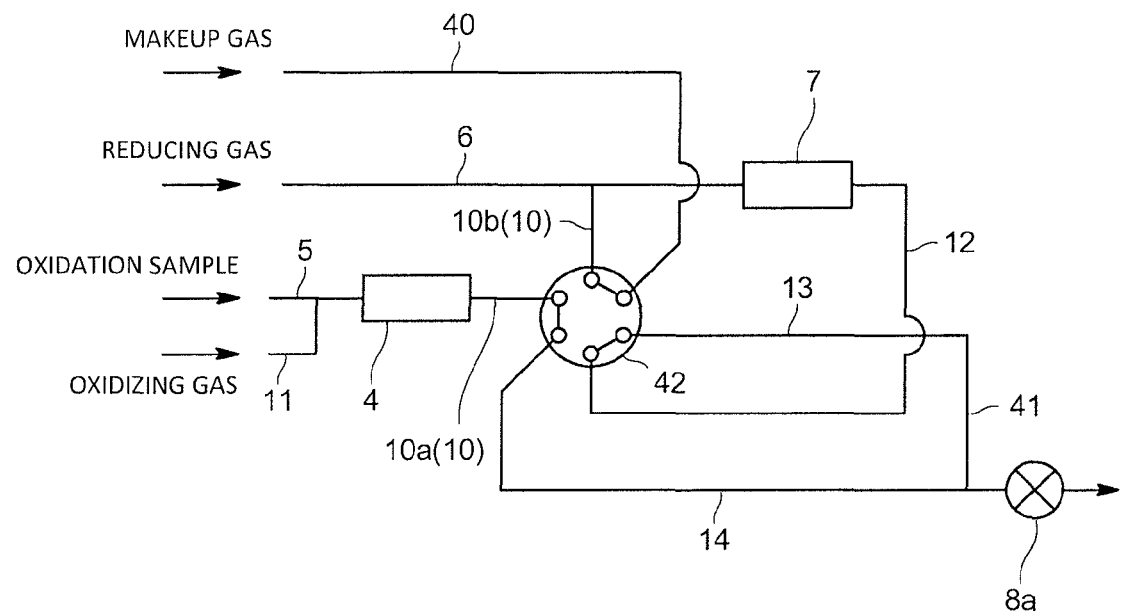

When the switching mechanism 42 switches to the first connection mode, as is shown in FIG. 5 (a), the first oxidation sample gas extraction pipe 10a is connected to the second oxidation sample gas extraction pipe 10b, the first makeup gas pipe 40 is connected to the second makeup gas pipe 41, and the first oxidation reduction sample gas extraction pipe 12 is connected to the analysis pipe 14.

Because of this, in the first connection mode, makeup gas is supplied directly to the analysis pipe 14 so that the flow velocity of the oxidation reduction sample gas flowing through the analysis pipe 14 is increased.

In contrast, when the switching mechanism 42 switches to the second connection mode, as is shown in FIG. 5 (b), the first oxidation sample gas extraction pipe 10a is connected to the analysis pipe 14, the first makeup gas pipe 40 is connected to the second oxidation sample gas extraction pipe 10b, and the first oxidation reduction sample gas extraction pipe 12 is connected to the second makeup gas pipe 41.

Because of this, in the second connection mode, because the first makeup gas pipe 40 and the second makeup gas pipe 41 are connected to the reduction reaction unit 7, makeup gas is supplied to the reduction reaction unit 7 together with reducing gas, and after passing through the reduction reaction unit 7, the makeup gas and the reducing gas are connected to the analysis pipe 14 and increase the flow velocity of the oxidation sample gas flowing through the analysis pipe 14.

In the gas chromatograph 1 of the fourth embodiment which has the above-described structure, because it is possible to use the makeup gas which is used in the flame ionization detector as the inert gas, compared with when inert gas is prepared separately, it is possible to prevent any adverse effects on the reduction reaction unit 7 and the concentration detection device 8a by means of a low-cost, simple structure.

Fifth Embodiment

Next, a gas chromatograph 1 according to a fifth embodiment of the present invention will be described. Note that the same symbols are used for portions that are the same as in the first embodiment, the second embodiment, the third embodiment, and the fourth embodiment, and any description of such portions is omitted.

The gas chromatograph 1 according to the fifth embodiment is another variant example of the gas chromatograph 1 of the fourth embodiment in that, instead of makeup gas being used by the flame ionization detector, hydrogen gas which is used as the fuel of the flame ionization detector is used. In addition, instead of the first makeup gas pipe 40 and the second makeup gas pipe 41, there are provided a first hydrogen pipe 50 and a second hydrogen pipe 51 along which hydrogen gas flows.

The switching mechanism 52 is provided with the same type of 6-way valve as in the third embodiment, and switches the connections between the first oxidation sample gas extraction pipe 10a, the second oxidation sample gas extraction pipe 10b, the first oxidation reduction sample gas extraction pipe 12, the analysis pipe 14, the first hydrogen pipe 50, and the second hydrogen pipe 51.

The first hydrogen pipe 50 and the second hydrogen pipe 51 are pipes along which the hydrogen that is used as a fuel by the flame ionization detector flows. An end portion on the upstream side of the first hydrogen pipe 50 is connected to a hydrogen supply unit (not shown), while an end portion on the downstream side thereof is connected to the 6-way valve. An end portion on the upstream side of the second hydrogen pipe 51 is connected to the 6-way valve, while an end portion on the downstream side thereof is connected to the analysis pipe 14.

Figure 6A:
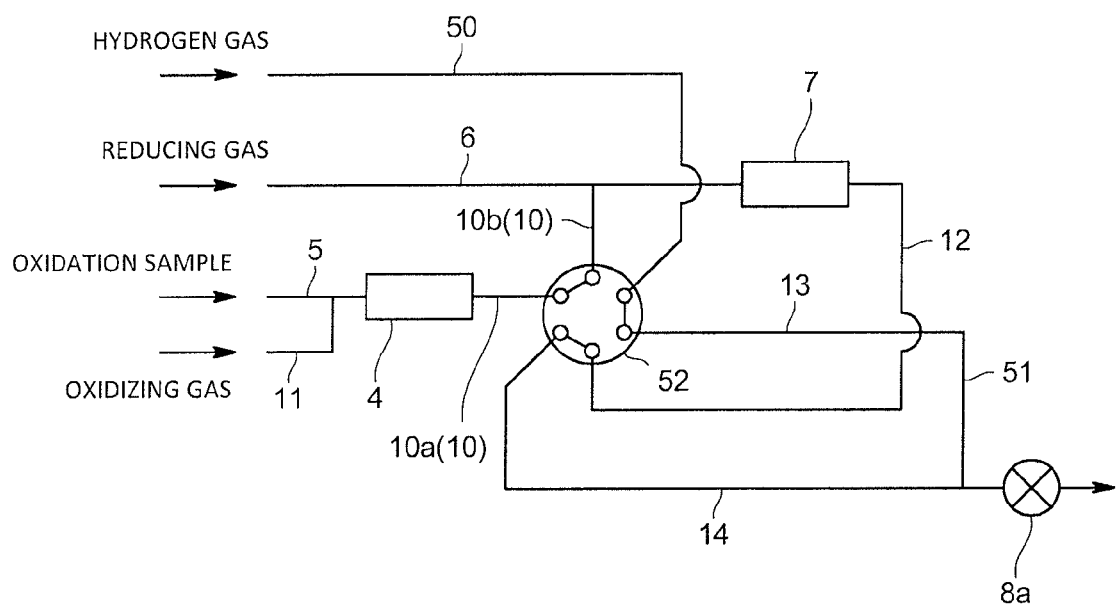
FIG. 6 (a) is an explanatory view showing a first connection mode in a gas chromatograph according to a fifth embodiment of the present invention.
Figure 6B:
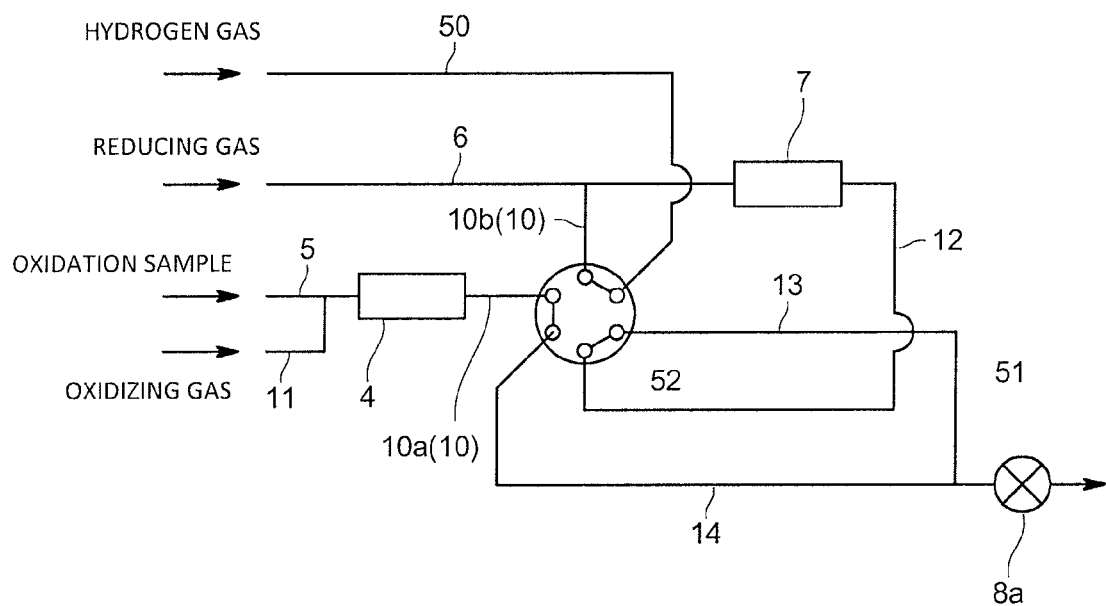
Figure 7:
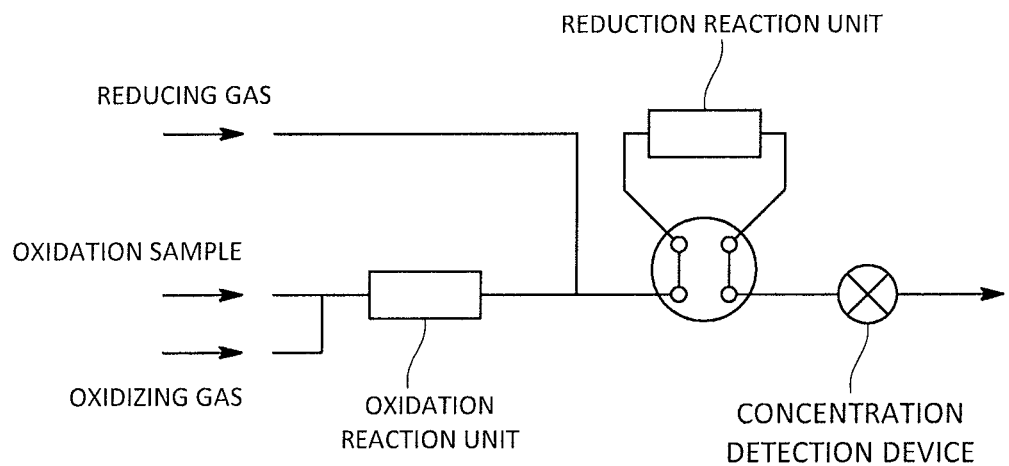
FIG. 7 (a) is an explanatory view showing a first connection mode in a conventional gas chromatograph.
Figure 7:
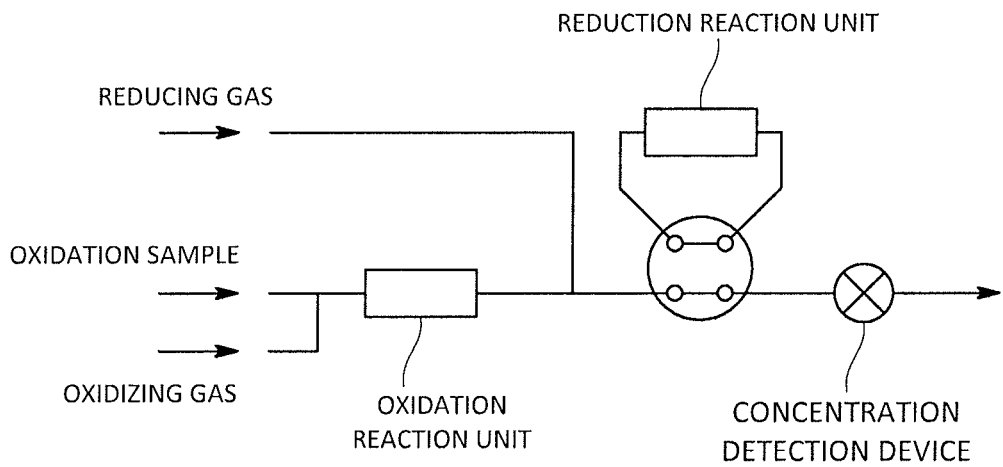

When the switching mechanism 52 switches to the first connection mode, as is shown in FIG. 6 (a), the first oxidation sample gas extraction pipe 10a is connected to the second oxidation sample gas extraction pipe 10b, the first hydrogen pipe 50 is connected to the second hydrogen pipe 51, and the first oxidation reduction sample gas extraction pipe 12 is connected to the analysis pipe 14.

Because of this, in the first connection mode, hydrogen gas is supplied directly as fuel to the flame ionization detector which is the concentration detection device 8a.

In contrast, when the switching mechanism 52 switches to the second connection mode, as is shown in FIG. 6 (b), the first oxidation sample gas extraction pipe 10a is connected to the analysis pipe 14, the second oxidation sample gas extraction pipe 10b is connected to the first hydrogen pipe 50, and the first oxidation reduction sample gas extraction pipe 12 is connected to the second hydrogen pipe 51.

Because of this, in the second connection mode, hydrogen gas and reducing gas are supplied to the reduction reaction unit 7, and after passing through the reduction reaction unit 7, the hydrogen gas and the reducing gas are supplied to the concentration detection device 8a. This hydrogen gas is used as fuel for the flame ionization detector which is the concentration detection device 8a.

The present invention is not limited to the above-described embodiments.

In the third embodiment and the fourth embodiment, in both the first connection mode and the second connection mode, the inert gas and the makeup gas flow respectively through the inert gas supply pipe and the first makeup gas supply pipe; however, it is also possible, for example, to provide a shut-off valve on the inert gas supply pipe or the first makeup gas supply pipe, and to open or close this shut-off valve to correspond to the timings when the switching mechanism switches to the first connection mode or the second connection mode. In this case, in the first connection mode, if the shut-off valve is closed, the flow volumes of the inert gas or makeup gas are reduced so that costs can be lowered.

Moreover, in the above-described embodiments, the second oxidation sample gas extraction pipe is connected to the reducing gas supply pipe; however, it is also possible for the second oxidation sample gas extraction pipe to be connected to the reduction reaction unit. Moreover, it is also possible for the oxidizing gas supply pipe to be connected to the oxidation reaction unit.

Furthermore, in addition to the above-described embodiments, it is also possible for a filter or trap that removes elements that obstruct analysis such as sulfur and the like to be connected to the first oxidation sample gas extraction pipe 10a, the oxidation reduction sample gas extraction pipe 12, or the analysis pipe 14 or the like.

Various modifications may also be made to the present invention insofar as they do not depart from the spirit or scope of the present invention.

INDUSTRIAL APPLICABILITY

The present invention makes it possible to provide a gas chromatograph in which any adverse effects on the reduction reaction unit that are caused by the degradation of the reduction catalyst, and any malfunctioning of the concentration detection device are prevented.

What is claimed is:
1. A gas chromatograph comprising:
   a column that, by causing a sample gas to pass through itself, is able to separate constituents to be measured that are contained in the sample gas;
   an oxidation reaction unit that, by using an oxidizing gas, oxidizes the sample gas that has passed through the column, and creates an oxidation sample gas;
   a reduction reaction unit that, by using a reducing gas, reduces the oxidation sample gas created by the oxidation reaction unit, and creates an oxidation reduction sample gas;
   an analyzing unit that analyzes the sample gas;
   a switch that switches modes of the gas chromatograph between
   a first connection mode in which the oxidation reaction unit is connected to the reduction reaction unit, and the reduction reaction unit is connected to the analyzing unit, and the oxidation reduction sample gas is introduced into the analyzing unit, and a second connection mode in which the oxidation reaction unit is connected to the analyzing unit, and the oxidation sample gas is introduced into the analyzing unit, and wherein the gas chromatograph further comprising a reducing gas supply pipe that, in both the first connection mode and the second connection mode, is connected to the reduction reaction unit and supplies the reducing gas to the reduction reaction unit, and the reducing gas supply pipe supplies the reducing gas with the oxidation sample gas after passing through the switch.

2. The gas chromatograph according to claim 1, wherein there is further provided an inert gas supply pipe that supplies inert gas to the reduction reaction unit.

3. The gas chromatograph according to claim 2, further comprising:

a control valve of the switch, in the first connection mode, configured to block the connection between the inert gas supply pipe and the reduction reaction unit, and in the second connection mode, the control valve is configured to connect the inert gas supply pipe and the reduction reaction unit to each other.

4. The gas chromatograph according to claim 1, wherein the analyzing unit has a flame ionization detector, and there is further provided a makeup gas supply pipe that supplies makeup gas to the analyzing unit, and a control valve of the switch, in the first connection mode, configured to block the connection between the makeup gas supply pipe and the reduction reaction unit, and in the second connection mode, the control valve is configured to connect the makeup gas supply pipe and the reduction reaction unit to each other.

5. The gas chromatograph according to claim 1, wherein the analyzing unit has a flame ionization detector, and the reducing gas is hydrogen.

* * * * *